(12) United States Patent
Hsu

(10) Patent No.: US 11,178,826 B1
(45) Date of Patent: Nov. 23, 2021

(54) CULTIVATION BAG ASSEMBLY FOR CULTIVATING MICROBES

(71) Applicant: Wei K. Hsu, Plano, TX (US)

(72) Inventor: Wei K. Hsu, Plano, TX (US)

(*) Notice: Subject to any disclaimer, the term of this patent is extended or adjusted under 35 U.S.C. 154(b) by 0 days.

(21) Appl. No.: 17/238,429

(22) Filed: Apr. 23, 2021

Related U.S. Application Data

(63) Continuation-in-part of application No. 17/218,721, filed on Mar. 31, 2021, now Pat. No. 11,066,632.

(51) Int. Cl.
*C12M 1/00* (2006.01)
*A01G 18/66* (2018.01)
*A01G 18/64* (2018.01)

(52) U.S. Cl.
CPC .......... *A01G 18/66* (2018.02); *C12M 23/14* (2013.01); *A01G 18/64* (2018.02)

(58) Field of Classification Search
CPC ......... C12M 23/14; A01G 18/64; A01G 18/66
See application file for complete search history.

(56) References Cited

U.S. PATENT DOCUMENTS

| | | |
|---|---|---|
| 3,865,695 A | 2/1975 | Massier |
| 4,878,312 A | 11/1989 | Shimizu |
| 4,977,702 A | 12/1990 | Fortin et al. |
| 5,230,430 A * | 7/1993 | Kidder .................. A01G 18/66 206/484.1 |
| 5,659,997 A | 8/1997 | Sprehe et al. |
| 6,358,731 B1 | 3/2002 | Hsu |
| 7,066,337 B2 | 6/2006 | Hsu |
| 8,001,718 B2 * | 8/2011 | Vandenhove .......... A01G 18/66 47/1.1 |
| 9,386,751 B2 * | 7/2016 | Creekmore .............. C12N 1/14 |
| 10,377,982 B1 | 8/2019 | Hsu |
| 2009/0197327 A1 * | 8/2009 | Bergmann .............. A01G 18/66 435/297.1 |
| 2015/0000188 A1 * | 1/2015 | Shirahane .............. A01G 18/64 47/1.1 |

FOREIGN PATENT DOCUMENTS

| | | |
|---|---|---|
| WO | WO2000023331 A2 | 4/2000 |
| WO | WO2021021696 A1 | 2/2021 |

* cited by examiner

*Primary Examiner* — Jonathan M Hurst
(74) *Attorney, Agent, or Firm* — Grady K. Bergen; Griggs Bergen LLP

(57) ABSTRACT

A cultivation bag assembly for the cultivation of microbes, fungi and other organisms includes an inner bag having first and second walls that are joined together along side edges to define an inner bag interior for containing a food substrate and an organism to be cultivated. At least one of the first and second walls is constructed of a layer of water-vapor permeable material to allow the passage of water vapor therethrough. An outer bag having first and second walls is joined along side edges to define an outer bag interior. The first and second walls of the outer bag are formed from gas impermeable layers. The inner bag and outer bag are coupled together at a first end of each of the inner bag and outer bag. The inner bag is contained within the interior of the outer bag in a cultivation configuration. A window is provided on the inner bag to allow one to view the interior of the inner bag through the window.

20 Claims, 7 Drawing Sheets

CULTIVATION BAG ASSEMBLY FOR CULTIVATING MICROBES

CROSS-REFERENCE TO RELATED APPLICATIONS

This application is a continuation-in-part of U.S. patent application Ser. No. 17/218,721, filed Mar. 31, 2021, which is incorporated herein by reference in its entirety.

FIELD OF THE INVENTION

The invention relates to cultivation bags for the cultivation of microbes, fungi, and other organisms, their manufacture and use.

BACKGROUND

With higher demand for organic products, methods for increasing the production of crops without the use of chemical fertilizers, pesticides and herbicides has been of particular interest and importance. Biopesticides used for agricultural purposes have been developed and continue to be developed to control pests and weeds, as well as act as fertilizers, thus increasing plant growth and crop yields without the need for chemicals that can damage the environment and cause safety and/or health concerns. These biological control agents are typically in the form of natural microbes, fungi, or other organisms, and in particular, fungi mycelium. These biological agents have a toxic effect on harmful insects and/or weeds, but do not negatively affect the growing crops, and/or may act beneficially as fertilizers that actually promote the growth of plants with which they are used.

The particular biological control agents used as pesticides act as parasitic microbes that attack the insects or undesirable plant matter causing them to die. By spreading these microbes or biological agents in the soil and fields, these materials can naturally destroy the damaging insects and/or weeds, as well as act as fertilizing agents to facilitate crop growth. Research and development is still underway in determining and isolating effective microbes and biological agents out of the many thousands that exist for use as such pesticides. Therefore their use is only expected to increase over time.

Of those parasitic microbes and organisms that are discovered and isolated for use as biopesticides, they must be produced in large quantities so that they can be used commercially for agricultural purposes. Once such system that is used by large industries involves produces the organisms in bulk. This involves the use of a large vessel containing a substrate. The substrate is a nutrient food source that a microbe, fungi, or particular organism prefers and when introduced into this substrate will tend to grow particularly rapidly on such substrate. In order to be used for cultivation the substrate must be sterilized to eliminate the growth of other undesirable microbes. To do this, the vessel with the substrate is typically heated to ≥121° C. for a certain length of time. This is typically accomplished with the use of live steam. The amount of time for sterilization depends on the amount of substrate being sterilized. After sterilization, the vessel and substrate are cooled. The pure, isolated microbe or biological agent, such as fungi mycelium, which may be previously grown in petri dishes or test tubes are then added to the substrate within the vessel. The vessel then slowly rotates and mixes the materials until they are homogenously mixed together.

Once the materials are mixed, the mixture is introduced into bags in suitable amounts and allowed to incubate at a desired temperature and humidity to promote growth of the particular microbes or other organisms. Incubation is typically complete when the substrate is completely consumed. Incubation is ended by drying the bag contents, which typically occurs under vacuum. After drying, the resulting dried microbial material is crushed and reduced in size to desired particles sizes.

While the large bulk processing systems are useful in producing large quantities of microbial materials useful as biopesticides, they have shortcomings. Such bulk systems are expensive and difficult to use, making them practical only for large producers. Furthermore, the bulk vessel is susceptible to contamination. If even one contamination spore enters the bulk vessel after sterilization, such as during introduction of the desired microbe that is being cultivated, the whole batch may be rendered unusable.

A more affordable method that can be used by smaller producers does not make use of a bulk vessel. Instead smaller plastic bags filled with substrate are used that can withstand the temperatures of sterilization (i.e., ≥121° C.) for a sufficient amount of time to sterilize the substrate. The bags may have a small filter to allow steam used for sterilization to escape during the sterilization procedure so that the bag does not explode or burst as it is heated. If no filter is used, the bag may be positioned upright with one end of the bag being open but with the opening restricted with either a foam or cotton wool material to allow the escape of steam.

Once the sterilized substrate is cooled, pure microbes or organisms to be cultivated are introduced into the bag. If a filtered bag is used, the open end is sealed, such as by welding. The bag and its contents are then agitated to mix the materials and the bag is placed on a shelf for incubation.

After incubation, the bag is cut open and the contents are poured into a second drying bag. Drying typically occurs with dry heating under a vacuum within a vacuum chamber for increased efficiency. Drying in bags is more suitable than in industrial drying, which involves higher temperatures, which can kill off the microbes that have been cultivated. The drying bag must be constructed to allow water vapor to readily escape while retaining the bag contents within the bag. Thus, the drying bag must have a large area of filter material to allow the water vapor to escape efficiently and quickly. The requirement of needing a second drying bag, however, adds additional costs and labor, as the ripe microbes from the incubation bag must be transferred to the drying bag to facilitate drying.

To overcome the shortcomings of the above-described methods, improvements are needed.

BRIEF DESCRIPTION OF THE DRAWINGS

For a more complete understanding of the disclosure, reference is now made to the following descriptions taken in conjunction with the accompanying figures, in which.

DETAILED DESCRIPTION

Figure 1:
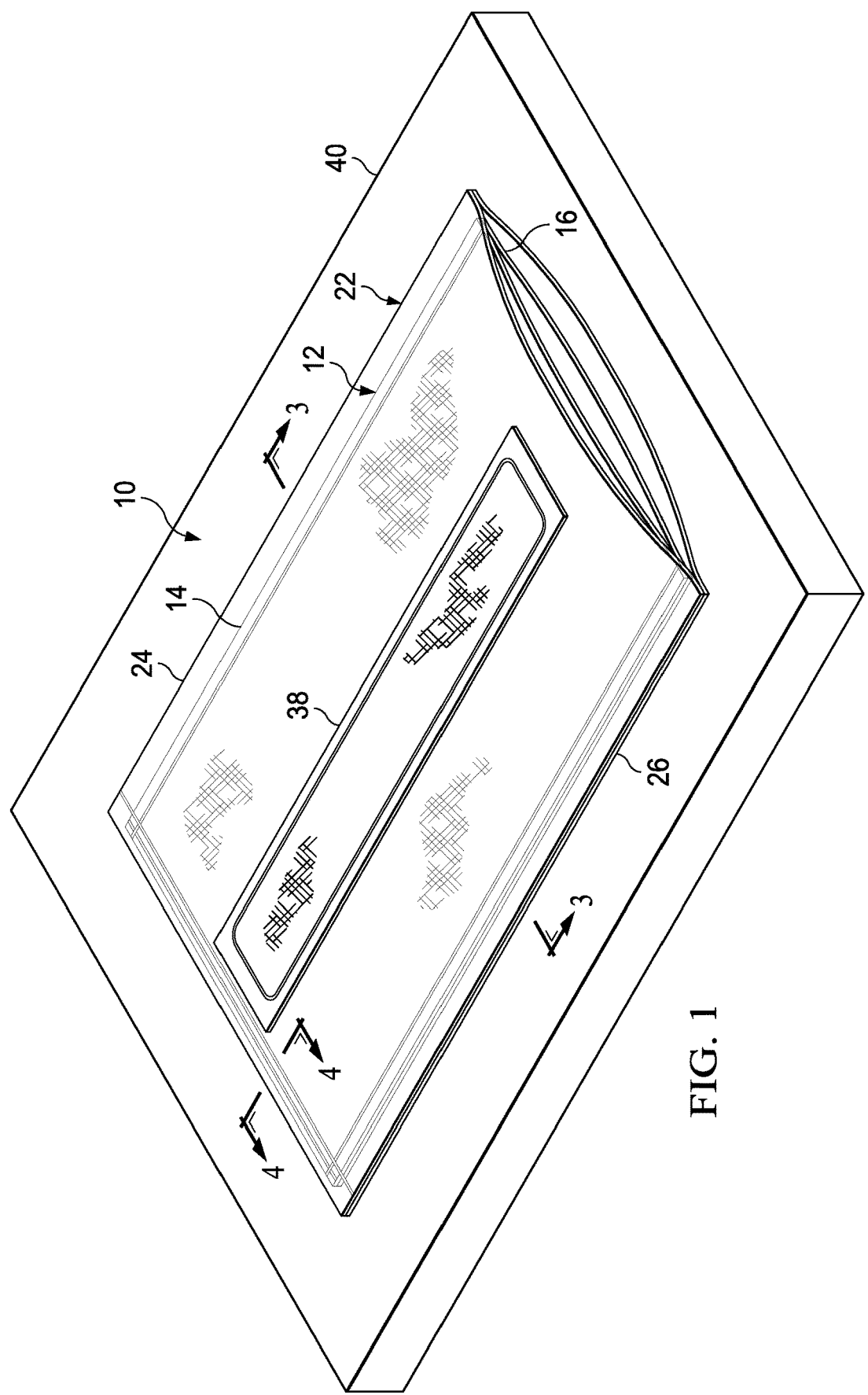
FIG. 1 is a perspective view of a cultivation bag assembly resting on a solid support surface and shown constructed in accordance with particular embodiments of the invention.

The control of pests by interference with their ecological status is achieved by introducing a natural enemy or a pathogen into the environment. This is also called biocontrol. In simple terms, parasites and agents that cause sickness to pests are introduced into the pests by natural means and cause the pests to die. The present invention is related to an improved cultivation bag assembly that has many advantages over the present art to reduce the steps in preparation and manufacture of these agents and to reduce risks of competing or contaminating matter introduced into to the process.

The bag assemblies of the invention are useful in cultivation through solid state fermentation. Solid state fermentation (SSF) can be defined as the growth of microorganisms in a moist solid substance in the absence of liquid water. The substance or substrate usually is composed of grain or grain waste, with addition of sugar, corn grits, rice wheat waste, potato waste. etc., which mimic the natural environment which the biological control agents grow in nature. SSF simulates the living conditions of filamentous fungi and is the biotechnological process of choice. Under favorable conditions, spore germination takes place through the formation of tubes which grow and will be the base of future mycelium. Through this process mycelium and spore production become the biocontrol agent. This agent infects and kills the pests once it is introduced into their environment.

As filamentous fungi grow hypha, which are the branching filaments that mycelium of the fungi, penetrate into the solid matrix, becoming impossible to separate substrate from mycelium. The biomass thus formed becomes the product to be dried and reduced in size so that it can be easily sprayed into fields or areas where the pests to be destroyed live. Most of the time this will be on vegetation that are planted in agriculture. It is therefore an advantage to stimulate maximum growth of filamentous fungi spores by allowing wet substrate contained in a bag and providing a breathing means through a filter. The filter is designed to allow gas exchange between the filamentous fungi in the substrate and ambient air by expelling $CO_2$ (carbon dioxide) generated in the bag and breathing in $O_2$ (oxygen). The filter will also have small enough pores to obstruct contaminating living matter to enter the bag and thus to consume and share the nutrients in the substrate. The amount of $CO_2$ in the bag is critical to optimum growth of filamentous fungi.

By placing the incubating bag under controlled conditions of temperature, ventilation, humidity and nutrients used, the substrate mass is totally consumed by the cultivated biological control agent. When the substrate mass is fully consumed, the bag contents are dried. In the prior art methods, this is done by removing the mass from the incubation bag and introducing it into a drying bag. The present invention eliminates this stage, however, since the incubation and drying bag are part of the same assembly.

In the drying process, drying air may be introduced into the environment and the large physical area of an underlying permeable material of the drying bag allows rapid dehydration of the biomass in the bag. When drying is completed, the drying bag is opened and the dried bio mass is reduced into particles that are further size reduced for packaging and marketing.

Referring to FIG. 1, a cultivation or incubation bag assembly 10 is shown for cultivating and drying microbes, fungi and other organisms, such as fungi mycelium, as discussed. The various components of the cultivation bag assembly 10 and its construction can be seen more readily in FIGS. 2 and 3. Additional illustrations showing particular embodiments of the cultivation assemblies constructed in accordance with the disclosed invention are also shown in copending U.S. Design Pat. application No. 29/780,036, filed Apr. 22, 2021, which is hereby incorporated by reference in its entirety for all purposes.

Figure 2:
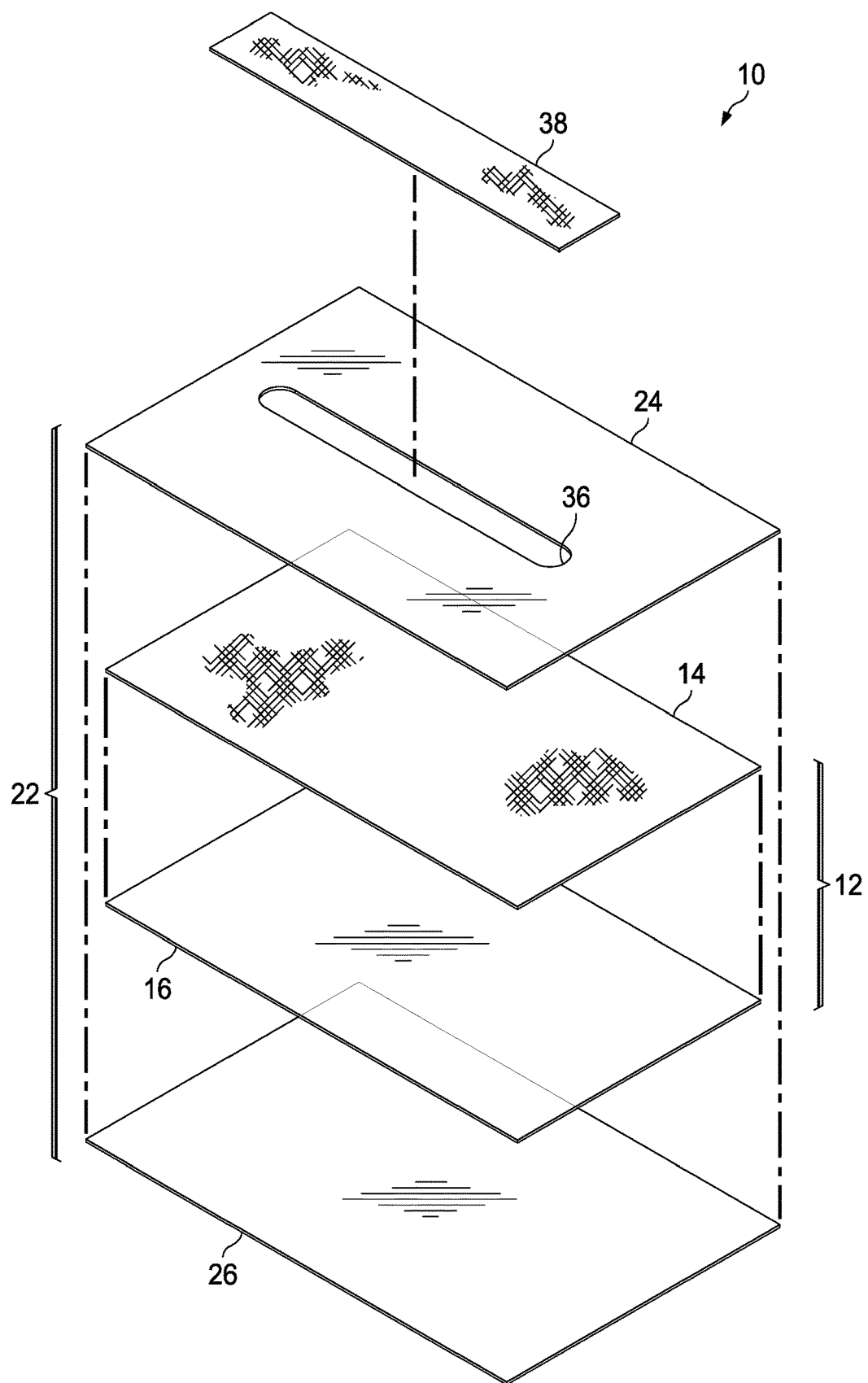
FIG. 2 is an exploded perspective view of the cultivation bag assembly of FIG. 1.
Figure 3:
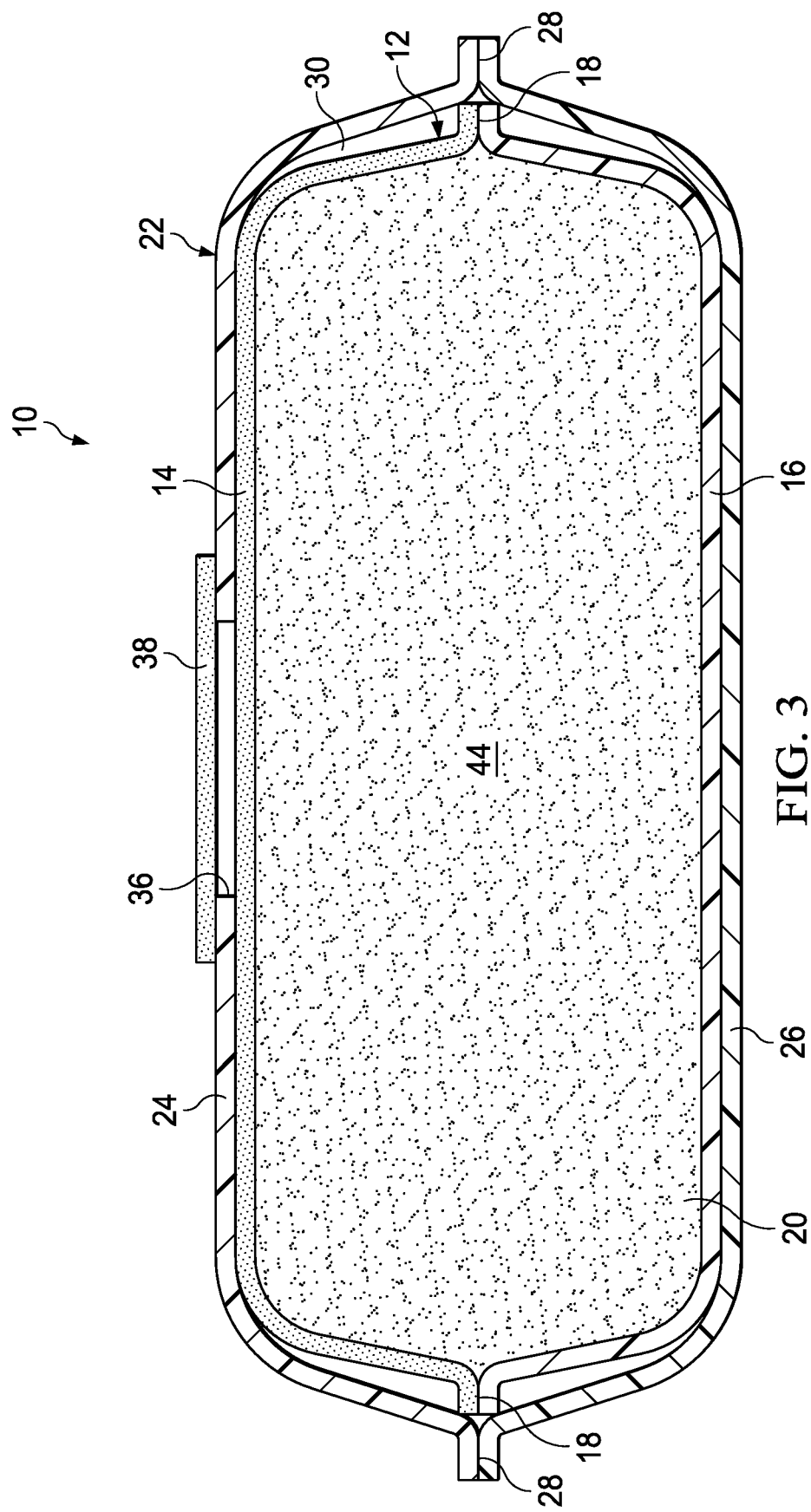
FIG. 3 is a cross-sectional view of cultivation bag assembly of FIG. 1 taken along the lines 3-3.

As shown in FIGS. 2 and 3, the bag assembly 10 includes multiple layers of material that are joined together to form the bag assembly 10. The bag assembly includes an inner drying bag 12 having flexible upper and lower walls 14, 16 joined around their perimeters along left- and right-side edges, such as at joint or seal 18 (FIG. 3) to define a bag interior 20 between the walls 14, 16. The front of the inner bag 12 may initially be open to allow for the introduction of a substrate material and a microbe, fungi, or other organism to be cultivated.

In the embodiment shown, all or a major portion of the upper wall 14 is formed from a layer of gas and water-vapor permeable material. The water-vapor permeable material of the upper wall 14 is constructed to allow the passage or transmission of air and other gases, as well as water vapor through the material of the upper layer 14. This may be a non-woven polyolefin fiber material, such as that sold under the name TYVEK®, available from E. I. du Pont de Nemours and Company, Wilmington, Del. The polyolefin fiber material of the upper wall may be polypropylene, polyethylene or high-density polyethylene (HDPE), or a combination of such materials. Examples of suitable commercially available products for the material of the upper wall 14 include, but are not limited to, TYVEK® 1025B, TYVEK® 1059B, and TYVEK® 1072B materials. The permeable material of wall 14 may have a perm rating of from 5 or greater to facilitate the passage of water vapor through the material. In particular embodiments, the water vapor transmission through the layer 14 may range from at least, equal to, and/or between any two 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 perms or more, in certain instance. The permeable material of wall 14 may be suitable for filtering out particles having a particle size of from 0.2 micron to 1 micron. Thus, the permeable material of wall 14 retains particles and powder of larger particle sizes within the inner drying bag 12. Such water-vapor permeable material materials are typically opaque or non-transparent so that they can not be readily seen through.

It should be noted in the description, if a numerical value, concentration or range is presented, each numerical value should be read once as modified by the term "about" (unless already expressly so modified), and then read again as not so modified unless otherwise indicated in context. Also, in the description, it should be understood that an amount range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific points within the range, or even no point within the range, are explicitly identified or referred to, it is to be understood that the inventor appreciates and understands that any and all points within the range are to be considered to have been specified, and that inventor possesses the entire range and all points within the range.

The lower wall 16 may be formed from the same or a similar permeable material as wall 14. If formed from the same material, the upper and lower walls 14, 16 may be formed by a single continuous sheet of such material by folding the sheet material along one edge so that the folded layers 14, 16 overlay one another. In such case, the seal, such as the seal 18, may be eliminated along such folded edge since the layers are effectively joined together along the fold line.

In the embodiment shown in FIG. 2, the lower wall 16 of inner bag 12 is formed from a separate layer of flexible film that may be gas impermeable so that water vapor and gases cannot pass or pass readily through the material of the film. All or a portion of such flexible film layer forming the lower wall 16 may be formed from a transparent or semitransparent material so that one can see through the lower wall 16 to see the contents of the inner bag 12. The layer 16 may be formed from a continuous thermoplastic film layer, such as the polyolefins of polypropylene, polyethylene or high-density polyethylene (HDPE). In certain embodiments, the upper and lower walls 14, 16 may be configured and joined together to provide gussets along the sides of the inner bag 12 so that the inner bag 12 is a gusseted bag.

In many applications, the material of the upper and lower wall layers 14, 16 may be of the same thermoplastic or polyolefin materials having the same or similar melting points, e.g., polypropylene, HDPE, etc., so that they may be joined together through heat or ultrasonic welding so that the materials are permanently or non-releasably fused together or otherwise strongly joined together so that they are not easily separated. In some instances, a different thermoplastic or polyolefin material having different melting points may be used to join the layers 14, 16 together. In other embodiments, other coupling means may be used to join the layers 14, 16 at seal 18 along the left- and right-side edges may be through the use of a strong adhesive layer positioned between the materials.

The bag assembly 10 further includes an outer incubation bag 22. The outer incubation bag 22 is sized and configured to receive and enclose the inner drying bag 12, including when the bag 12 is filled with substrate material and a microbe, fungi, or other organism to be cultivated. The outer bag 22 has flexible upper and lower walls 24, 26 joined around their perimeters along left- and right-side edges, such as at seam or seal 28 (FIG. 3) to define a bag interior 30 between the walls 24, 26. The forward end of the outer bag 22 may initially be open to allow access to the forward end and opening 32 (FIG. 4) of the inner bag 12. The left- and right-side edges of the inner bag 12 are free from or non-coupled to the outer bag 22.

The upper and lower walls 24, 26 of outer bag 22 may each be formed from a layer of flexible film that may be gas impermeable so that water vapor and gases cannot pass or pass readily through the material of the film. The layers 24, 26 may be transparent, semitransparent, opaque or non-transparent and may each be formed from a continuous thermoplastic film layer or sheet, such as the polyolefins of polypropylene, polyethylene or high-density polyethylene (HDPE). In certain embodiments, the upper and lower walls 24, 26 may be configured and joined together to provide gussets along the sides of the outer bag 22 so that the outer bag 22 is a gusseted bag. In many applications, all or a portion of the layers 24, 26 will be transparent or semitransparent so that one can look through the sheet material of the layer 24, 26 to see the inner bag 12.

In many applications, the material of the upper and lower wall layers 24, 26 may be of the same thermoplastic or polyolefin materials having the same or similar melting points, e.g., polypropylene, HDPE, etc., so that they may be joined together through heat or ultrasonic welding so that the materials are permanently or non-releasably fused together or otherwise strongly joined together so that they are not easily separated. If formed from the same material, the upper and lower walls 24, 26 may be formed by a single continuous sheet of such material by folding the sheet material along one edge so that the folded layers 24, 26 overlay one another. In such case, the seal, such as the seal 28, may be eliminated along such folded edge since the layers are effectively joined together along the fold line.

Figure 4:
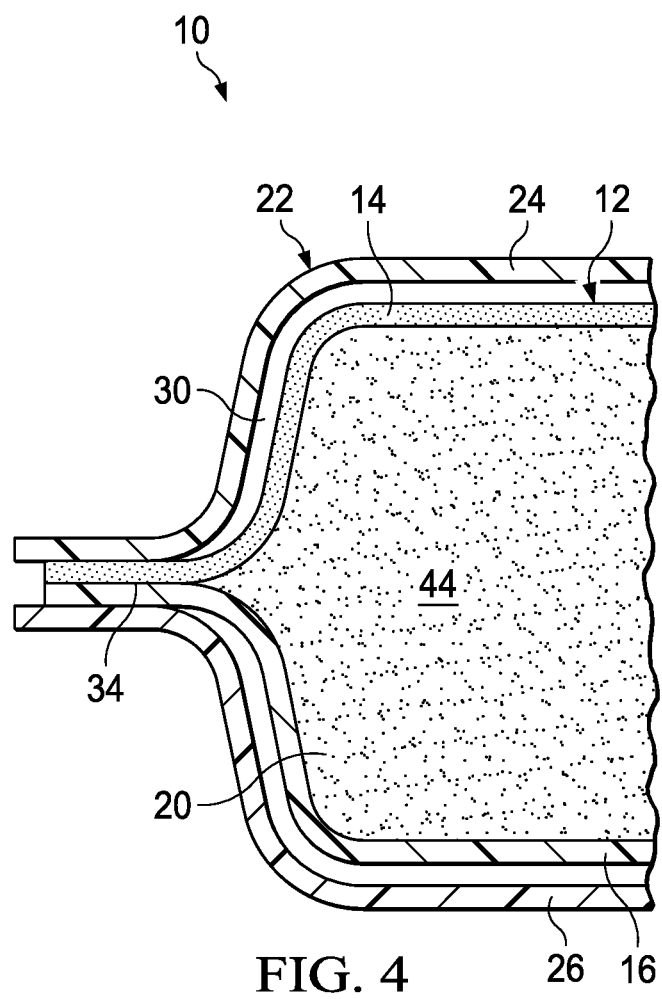
FIG. 4 is a cross-sectional view of cultivation bag assembly of FIG. 1 taken along the lines 4-4

Referring to FIG. 4, the rearward end of the inner bag 12 is coupled together to the rearward end of the outer bag 22. This may be one or more transverse seams or seals 34 that extend across all or a portion of the width of the each of the rearward ends of the inner and outer bags 12, 22. As can be seen, the rearward end edges of the upper and lower walls 14, 16 of the inner bag 12 may be sandwiched between the rearward end edges of the upper and lower walls 24, 26 of the outer bag 22. This seam or seal 34 also serves to couple the upper and lower layers 14, 16 of the inner bag 12 to effectively close off the rearward end of the inner bag 12. Likewise, the rear end edges of the upper and lower walls 24, 26 of the outer bag 22 are coupled along the rear end edges of the upper and lower walls 14, 16 along seam or seal 34 to effectively close off the rearward end of the outer bag 22.

In some embodiments, the materials of one or both of the upper and lower walls 14, 16 of the inner bag 12 and one or both of the upper and lower walls 24, 26 of the outer bag 22 may be formed from the same thermoplastic or polyolefin materials having the same or similar melting points, e.g., polypropylene, HDPE, etc. This may allow the layers to be joined together through heat or ultrasonic welding so that the materials are permanently or non-releasably fused together or otherwise strongly joined together so that they are not easily separated. In some instances, a different thermoplastic or polyolefin material having different melting points may be used to join one or both of the layers 14, 16 of the inner bag 12 together and/or to one or both of the upper and lower layers 24, 26 of the outer bag 22 along seal 34. In other embodiments, other coupling means may be used to join the layers 14, 16, 24, 26 to one another along seal 34 along the rearward end edges may be through the use of a strong adhesive layers positioned between the materials for permanent or non-releasable coupling.

In some instances, a different thermoplastic or polyolefin material having different melting points or other properties may be used for one or both of the upper and lower walls 14, 16 of the inner bag 12 from that of one or both of the upper and lower walls 24, 26 of the outer bag 22. This difference in melting points or properties of the different materials forming the layers 14, 16, 24, and 26 allows the materials to be releasably coupled together. In certain embodiments, the difference in melting points between the different materials used to provide the releasability may be from 10° C., 20° C., 30° C., 40° C., 50° C. or more. Thus, for example, the layers 14, 16 of the inner bag 12 may be constructed of polypropylene, which may have a melting point of from 130° C. to 171° C. The layers 24, 26 of the outer bag 22, however, may be formed from HDPE, which may have a melting point of from 115° C. to 135° C. Because of the different materials used and their different melting points and/or properties, the materials are not as strongly held together along seal or seam 34 as they would be if they were formed from the same materials. This low bonding strength may aid or facilitate the releasability of the layers 14, 16, 24, 26 from one another along seam 34, as will be discussed later on. In other instances, the use of a releasable adhesive may be used to join the layers 14, 16, 24, 26 along seam 34. This may be a continuous layer of adhesive that effectively seals and releasably joins the layers together.

Referring to FIG. 2, an opening or slot 36 is formed in the upper wall 24 of the outer incubation bag 22 at a position so that the opening 36 directly overlays the permeable layer of the upper wall 14 of inner bag 12 when the inner drying bag 12 is positioned within the outer cultivation bag 22. The opening or slot 36 is shown as being an elongated slot that extends along a major portion of the length of the upper wall 24. The opening 36 is smaller in area than the permeable upper wall 14 so that only a portion of the upper wall 14 underlies the opening 36.

A gas filter patch 38 is coupled to the upper wall 24 and is used to cover the opening 36. The gas filter patch 38 is an incubation filter that allows the optimum gas exchange into the interior 30 of the outer incubation bag 22 and into the interior 20 of the inner drying bag 12. This involves the passage of air and/or oxygen and carbon dioxide gases to and from ambient air, as well as some water vapor, to facilitate cultivation. The gas filter patch 38 may a non-woven polyolefin fiber material. There are many commercially available materials useful for the filter patch 38, which may be formed from non-woven polypropylene or HDPE. The filter patch material will typically have smaller openings than that used for the permeable layer of upper wall 14 of inner drying bag 12. In particular applications, the filter patch 38 may be suitable for filtering out particles having a particle size of from 0.01 micron to 0.2 micron or greater. The filter patch 38 and the corresponding opening 36, in conjunction with the porosity of the filter patch 38, may be sized and configured to allow the selected passage of air, oxygen and carbon dioxide, and some water vapor, for the particular organism being cultivated. Thus, the size and configuration of the filter patch 38 and opening 36 may vary depending on the purpose, use, and environmental conditions (i.e., the type of organism being cultivated and its cultivating environment) of the bag assembly 10.

The side edges of the filter patch 38 are coupled or joined to the upper layer 24 of the outer bag 22, around the entire perimeter of the opening 36 so that the opening 36 is completely covered by the filter patch 38. In many applications, the material of the upper film layer 24 and the filter patch layer 38 may be of the same thermoplastic or polyolefin material having the same or similar melting points, e.g., polypropylene or HDPE, so that they may be joined together through heat or ultrasonic welding so that the materials are permanently or non-releasably fused together or otherwise strongly joined together so that they are not easily separated. In other embodiments, other coupling means may be used to join the filter patch 38 to the film layer 24, such as through the use of a strong adhesive layer positioned between the materials.

In forming the bag assembly 10, the layers 14, 16 of the inner bag 12 are coupled together along their left- and right-side edges along the length of the layers 14, 16. This may be done by heat or ultrasonic welding, as previously discussed, so that the materials are permanently or non-releasably fused together or otherwise strongly joined together. Alternatively, a strong adhesive may be used to couple the layers 14, 16. In manufacturing, long, continuous lengths of the sheet material forming the layers 14, 16 may be coupled together in this fashion with the seams or seals 18 extending along the continuous length of the layers. The coupled layers may then be cut transversely to the desired length to form several of the individual inner bags 12. At this stage the forward and rearward ends of the inner bag 12 remain open.

Likewise, the layers 24, 26 of the outer bag 22 are coupled together along their left- and right-side edges along the length of the layers 24, 26. This may also be done by heat or ultrasonic welding, as previously discussed, so that the materials are permanently or non-releasably fused together or otherwise strongly joined together. Alternatively, a strong adhesive may be used to couple the layers 24, 26. In manufacturing, long, continuous lengths of the sheet material forming the layers 24, 26 may be coupled together in this fashion with the seams or seals 28 extending along the continuous length of the layer materials. The coupled layers may then be cut transversely to the desired length to form several of the individual outer bags 22. At this stage the forward and rearward ends of the outer bag 22 also remain open.

The thus formed inner bag 12 is positioned within the interior of the outer bag 22. The inner bag 12 will typically have a smaller width and length than the outer bag 22 to facilitate fitting and positioning of the inner bag 12 within the outer bag 22. With the inner bag 12 positioned within the interior of the outer bag, the inner and outer bags 12, 22 are coupled together at their rearward ends along transverse seal or seam 34, as previously discussed, so that each of the rearward ends of the inner and outer bags 12, 22 are effectively closed and the inner bag 12 is coupled to the outer bag 22 along the seam 34. In this configuration, each of the upper and lower walls 14, 16 and 24, 26 of the inner and outer bags 12, 24 will project forward from the seam or seal 34 in the same direction, with the inner bag 12 being contained within the outer bag 22.

Figure 5:
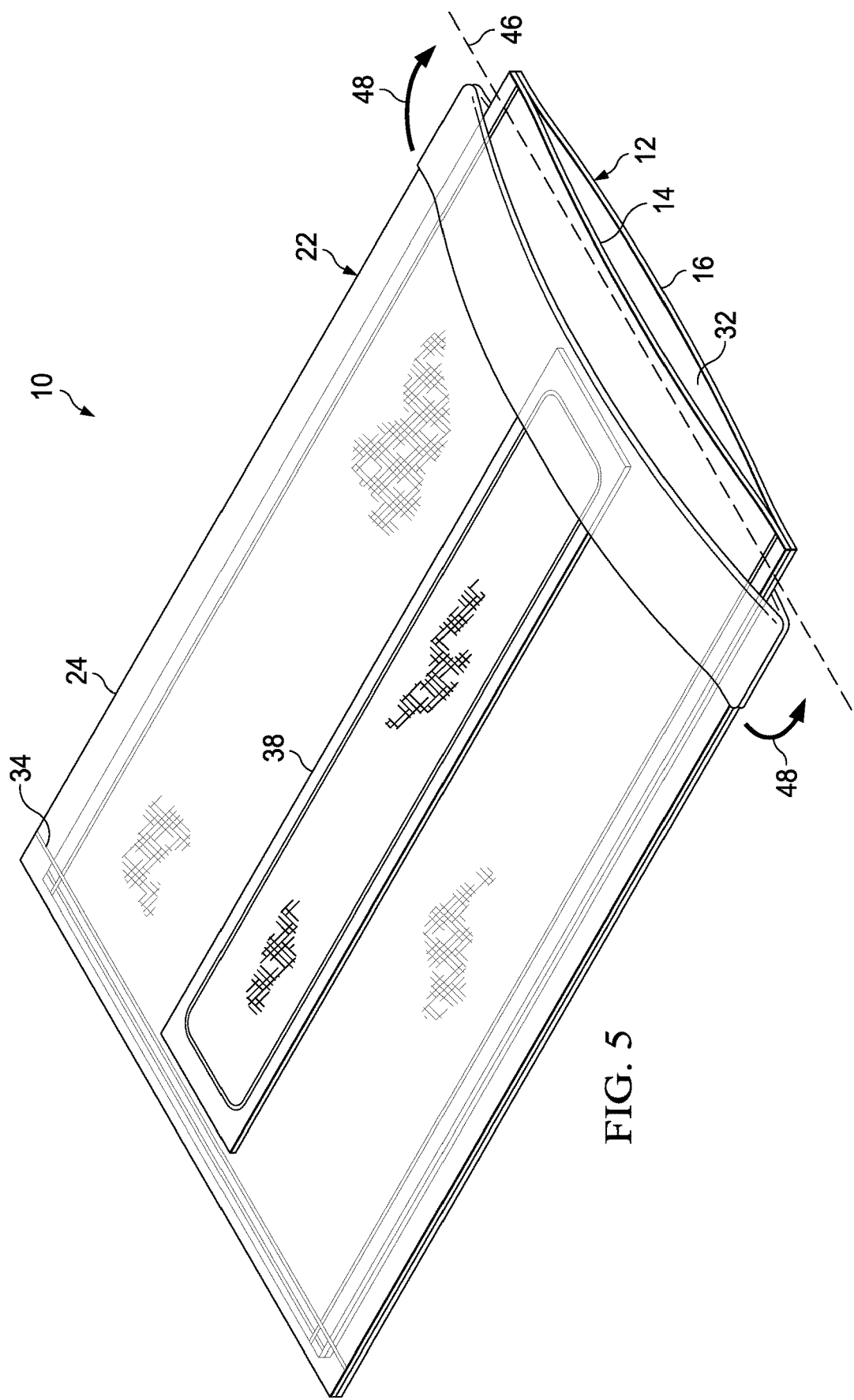
FIG. 5 is a perspective view of the cultivation bag assembly of FIG. 1 shown with the forward end of an outer bag of the bag assembly folded back to access the forward end of an inner bag of the bag assembly.

As shown in FIG. 5, the end portions of layers 24, 26 forming the open forward end of the outer bag 22 are initially folded back upon themselves so that the forward end of the inner bag 12 projects out a distance beyond the forward opening of the outer bag 22. In this configuration, the forward end of the inner bag 12 is open with the front-end edges of the upper and lower walls 14, 16 not being joined together to define the opening 32 of the inner bag 12. This allows for the introduction of a food substrate, along with microbes, fungi or other organisms, such as fungi mycelium, to be cultivated, such as shown at 44 of FIGS. 3 and 4, into the inner bag interior 20. The food substrate is typically an organic material that provides nutrients and moisture for the cultivation of the desired microbe or organisms. The substrate may be wet or dry. One suitable type of substrate useful for the cultivation of fungi mycelium is wet rice. Other substrate materials may also be used, however, and may vary based upon the organism being cultivated.

The bag assembly 10, including any substrate, may be sterilized or fabricated under sterile conditions to prevent contamination of the cultivated organisms. If the materials can withstand heat sterilization, heat sterilization may be used. Heat sterilization may be used by heating the bag assembly 10 and/or its components, with or without any substrate, to a temperature of from 121° C. or higher to effectively kill any unwanted bacteria, viruses or other undesirable microorganisms.

Because components of the bag assembly 10 may be constructed of different thermoplastic materials, such as HDPE, which may have a lower melting point that would degrade the material if such high temperatures were used, other non-heat sterilization techniques may need to be used. This may include radiation, such as gamma radiation, or chemical sterilization. In such instances, the bag assembly 10, with or without any substrate, is subjected to radiation or sterilization chemicals to effectively sterilize the bag assembly and any substrate contained therein.

Once the bag assembly 10 and substrate are sterilized, pure microorganisms, fungi or other organisms to be cultivated are introduced into the interior 20 of the inner bag 12 through opening 32. This may be done in sterile or clean room conditions to avoid any contamination of the materials.

With the food substrate and microbe, fungi or organisms to be cultivated located within the interior 20 of the inner bag 12, the layers 14, 16 can be joined or coupled together at their forward end edges across their widths, such as along dashed line 46, so that the opening 32 is sealed or closed and these materials are enclosed within the interior 20 of the inner bag 12. This may be through heat or ultrasonic welding so that the materials are permanently or non-releasably fused together or otherwise strongly joined together so that they are not easily separated. In other embodiments, other coupling means may be used to join the end edges of the layers 14, 16 together, such as through the use of a strong adhesive layer positioned between the materials.

The forward end edges of the layers 24, 26 of the outer bag are then unfolded, such as shown by the arrows 48, so that the layers 24, 26 cover the now closed end of the inner bag 12. The unfolded ends of layers 24, 26 can then be joined or coupled together at their forward ends across their widths, so that the forward opening of the outer bag 22 is closed and the inner bag 12 is contained enclosed within the interior 30 of the outer bag 22 in a cultivation configuration of the bag assembly 10. The joining of the layers 24, 26 at their forward ends may be through heat or ultrasonic welding so that the materials are permanently or non-releasably fused together or otherwise strongly joined together so that they are not easily separated. In other embodiments, other coupling means may be used to join the forward end edges of the layers 24, 26 together, such as through the use of a strong adhesive layer positioned between the materials.

After the bag assembly 10 is filled and sealed, the bag assembly 10 and its contents may then be agitated to thoroughly mix the contents within the bag assembly. With the cultivation bag assembly 10 sealed and the contents mixed, the bag assembly 10 and its contents are placed in an environment (e.g., temperature, humidity, light, etc.) suitable for growing and cultivation. As shown in FIG. 1, the bag assembly 10 may be placed upon a solid shelf or support surface during cultivation, such as the support surface 40. The support surface 40 may be solid plastic, stainless steel, wood, concrete, etc. The bag assembly 10 may also be used over a non-solid or vented surface during cultivation, such as the grating 42 of FIG. 6. This may facilitate drying during the drying step, which is discussed later. During cultivation, the gas filter patch 38 positioned over the opening 36 of the upper wall 24 of outer bag 22 is exposed and allows the optimum gas exchange into the interior 30 of the outer bag 22 and through the permeable upper wall 14 into the interior 20 of the inner bag 12 where the substrate and cultivated organisms are located. This involves the passage of air and/or oxygen and carbon dioxide gases to and from ambient air, as well as some water vapor, to facilitate cultivation.

When the cultivated organisms are ripe, which is typically after all of the substrate has been consumed by the cultivated organism, the bag assembly contents are dried. As discussed earlier, in prior art methods, this would typically occur by emptying the contents of the cultivation bag into a separate drying bag. With the bag assembly 10 of the invention, however, this is not needed as both cultivation and drying can be accomplished using the same bag assembly.

Figure 6:
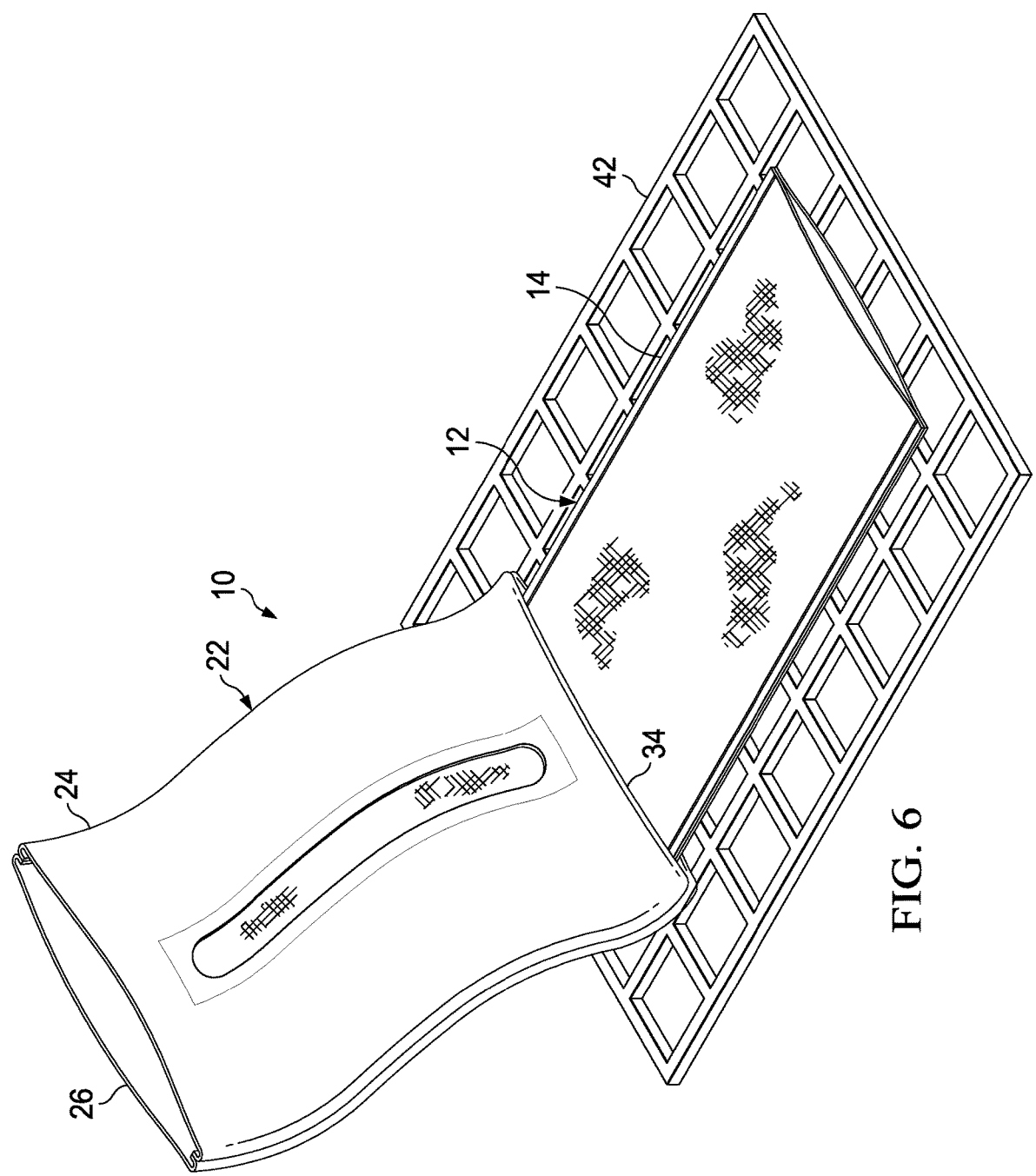
FIG. 6 is a perspective view of the cultivation bag assembly of FIG. 1 shown resting on a grate with the outer bag pulled away from the inner bag during a drying operation.

To dry the bag assembly contents, the outer bag 22 is opened at the forward end and pulled back away from the inner bag 12 so that the inner bag 12 is exposed in a drying configuration of the bag assembly 10, as shown in FIG. 6. In this drying configuration, the upper and lower walls 24, 26 of the outer bag 22 will be folded back over the seal or seam 34 that couples the inner bag 12 and outer bag 22 together so that the inner bag 12 is no longer contained within the interior of the outer bag 22 and the outer bag 22 is now folded inside out. Water vapor passes through the water-vapor permeable upper layer 14 of the inner bag 12, to facilitate drying. In many applications, the drying may be conducted with heating and/or under vacuum within a vacuum chamber to speed up drying. In applications, where the bag assembly 12 is used on a grating, such as grating 42 of FIG. 6, the lower wall 16 of the inner bag may also be formed from a permeable material, such as the permeable material of the upper wall 14, to further facilitate drying.

During drying, the outer bag 22 may remain coupled at its rearward end along seam 34 to the rearward end of the inner bag 12 but be moved to a position so that the permeable upper wall 14 of the inner bag 12 remains exposed to facilitate drying. In other embodiments, however, the outer bag 22 may be removed completely from the inner bag 12. In such instances, the materials of the outer bag 22 may be coupled to the materials of the inner bag 12 with a low bond strength to facilitate removal of the outer bag 22. This may be accomplished by using different materials having different melting points for the upper and lower walls 14, 16 of the inner bag 12 and the upper and lower walls 24, 26 of the outer bag 22, as discussed previously. The difference in melting points or properties of the different materials forming the layers 14, 16 and 24, 26 creates a low bonding strength that allows the materials to be releasably coupled together. In other instances, the use of a releasable adhesive may be used to join the layers 14, 16 and 24, 26 along seam 34. This may be a continuous layer of adhesive that effectively seals and releasably joins the layers together. Alternatively, the outer bag 22 may be cut away from the inner bag 12 if it is no longer needed.

After drying, the inner drying bag 12 of the bag assembly 10 and its contents may be agitated to break the materials located within into smaller particles. The inner bag 12, with or without the outer bag 22, and its contents may then be packaged, shipped and/or stored for later use as biopesticide or biological agent that can be spread on agricultural plots for growing crops for controlling pests, weeds or for use as a fertilizer, as described earlier. The inner bag 12 and bag assembly 10 is made of durable materials so that it can be used for shipping and storage without having to unseal and remove the contents and placing them in a different bag prior to use.

Figure 7:
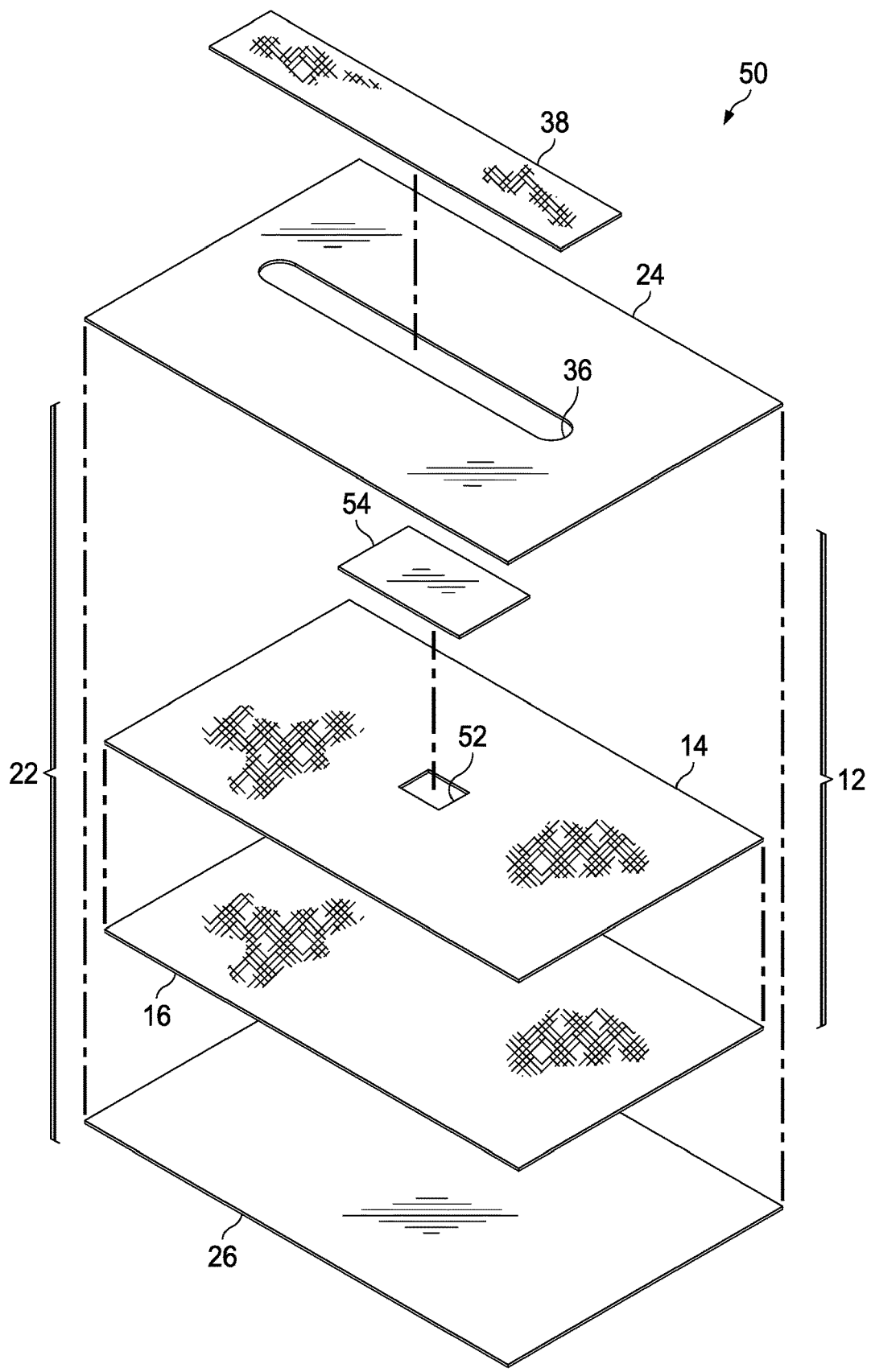
FIG. 7 is an exploded perspective view of another embodiment of a cultivation bag assembly that includes a window formed in an inner bag of the bag assembly.

Referring to FIG. 7, another embodiment of a cultivation bag assembly 50 is shown. The cultivation bag assembly 50 is constructed similarly to the cultivation bag assembly 10, with similar components labeled with the same reference numerals.

As shown, the bag assembly 50 differs from the bag assembly 10 in that the lower layer 16 of the inner bag 12 is formed from a gas and water-vapor permeable layer, such as that previously described for the upper layer 14 of bag assembly 10. Such upper and lower layers 14, 16 may be non-transparent or opaque so that one cannot see the through the walls 14, 16 of the inner bag 12 to view the contents within the inner bag 12.

In the bag assembly 50, an opening 52 is formed in the upper wall 14. A layer of transparent material 54, such as a transparent film, overlays the opening 52 and is coupled to the upper wall 14 along its side edges to close off the opening 52. If desired, a similar opening and transparent layer (not shown) may be provided with the lower wall 16. The opening 52 is formed in only a small area of the upper wall 14. The area of the window or opening 52 may be from 20%, 19%, 18%, 17%, 16%, 15%, 14%, 13%, 12%, 11%, 10%, 9%, 8%, 7%, 6%, 5% or less of the total area of the upper wall 14. The opening 52 and transparent layer 54 form a window so that one can view the interior of the inner bag 12 through the wall 14 and/or wall 16, if a window is provided on the lower wall 16.

The transparent layer 54 may be the same material as the upper and lower walls 14, 16, such as the same thermoplastic or polyolefin materials having the same or similar melting points, e.g., polypropylene, HDPE, etc. This may allow the layers to be joined together through heat or ultrasonic welding so that the materials are permanently or non-releasably fused together or otherwise strongly joined together so that they are not easily separated. In other embodiments, the transparent layer 54 may be formed from a different thermoplastic or polyolefin material.

The manufacture and use of the bag assembly 50 is similar to that previously described for bag assembly 10.

While the invention has been shown in only some of its forms, it should be apparent to those skilled in the art that it is not so limited but is susceptible to various changes and modifications without departing from the scope of the invention. Accordingly, it is appropriate that the appended claims be construed broadly and in a manner consistent with the scope of the invention.

I claim:

1. A cultivation bag assembly for the cultivation of microbes, fungi and other organisms comprising:
    an inner bag having first and second walls that are joined together along side edges to define an inner bag interior for containing a food substrate and an organism to be cultivated, at least one of the first and second walls being constructed of a layer of water-vapor permeable material to allow the passage of water vapor therethrough; and
    an outer bag having first and second walls joined along side edges to define an outer bag interior, the first and second walls of the outer bag being formed from gas impermeable layers, at least one of the first and second walls of the outer bag having an opening with a gas filter patch covering the opening to allow the passage of oxygen and carbon dioxide gases through the gas filter patch to and from ambient air and into and out of the interior of the inner bag to facilitate incubation of the organism within the interior of the inner bag, and wherein the inner bag and outer bag are coupled together at a first end of each of the inner bag and outer bag, with the inner bag being contained within the interior of the outer bag in a cultivation configuration; and wherein
    at least one of the first and second walls of the inner bag is non-transparent or opaque, said at least one of the first and second non-transparent or opaque walls of the inner bag having a window to allow one to view the interior of the inner bag through the window.

2. The bag assembly of claim 1, wherein:
    both first and second walls of the inner bag are each constructed of a layer of non-transparent or opaque water-vapor permeable material.

3. The bag assembly of claim 2, wherein:
    the layer of non-transparent or opaque water-vapor permeable material is constructed from a non-woven polyolefin fiber material.

4. The bag assembly of claim 1, wherein:
    the inner bag and outer bag are coupled together at the first end to close the first end of each of the inner bag and outer bag.

5. The bag assembly of claim 1, wherein:
    the outer bag and the inner bag are formed from at least one of polypropylene, polyethylene, and high density polyethelene (HDPE).

6. The bag assembly of claim 1, wherein:
    the side edges of the inner bag are non-coupled to the outer bag.

7. The bag assembly of claim 1, wherein:
    the bag assembly is a sterilized bag assembly.

8. The bag assembly of claim 1, wherein:
    the water-vapor permeable material has a perm rating of from 5 or greater.

9. The bag assembly of claim 1, wherein:
    a second end of each of the inner bag and the outer bag are non-coupled together.

10. The bag assembly of claim 9, wherein:
    the interior of the inner bag contains at least one of microbes, fungi and other organisms to be cultivated together with a food substrate, with the first and second walls of the inner bag being joined together at the second end of the inner bag to enclose said at least one of microbes, fungi and other organisms and food substrate within the interior of the inner bag; and wherein the first and second walls of the outer bag are joined together at the second end of the outer bag to enclose the inner bag within the interior of the outer bag.

11. The bag assembly of claim 1, wherein:
    the window is formed from an opening formed in said at least one of the first and second non-transparent or opaque walls of the inner bag and a layer of transparent material that overlays the opening and is coupled to said at least one of the first and second non-transparent or opaque walls of the inner bag.

12. The bag assembly of claim 1, wherein:
    the area of the window is from 20% or less of the total area of said at least one of the first and second non-transparent or opaque walls of the inner bag.

13. A method of forming a cultivation bag assembly for the cultivation of microbes, fungi and other organisms comprising:
    forming an inner bag having first and second walls that are joined together along side edges to define an inner bag interior for containing a food substrate and an organism to be cultivated, at least one of the first and second walls being constructed of a layer of water-vapor permeable material to allow the passage of water vapor therethrough, at least one of the first and second walls of the inner bag is non-transparent or opaque;

providing a window in said at least one of the first and second non-transparent or opaque walls of the inner bag to allow one to view the interior of the inner bag through the window;

forming an outer bag having first and second walls joined along side edges to define an outer bag interior, the inner bag being contained within the interior of the outer bag, the first and second walls of the outer bag being formed from gas impermeable layers, at least one of the first and second walls of the outer bag having an opening with a gas filter patch covering the opening to allow the passage of oxygen and carbon dioxide gases through the gas filter patch to and from ambient air and into and out of the interior of the inner bag to facilitate incubation of the organism within the interior of the inner bag; and coupling the inner bag and outer bag together at a first end of each of the inner bag and outer bag to close the first end of each of the inner bag and outer bag.

14. The method of claim 13, wherein:

each of the inner bag and outer bag has an open second end; and further comprising:

introducing at least one of microbes, fungi and other organisms to be cultivated together with a food substrate into the interior of the inner bag through the open second end of the inner bag;

joining the first and second walls of the inner bag together at the second end of the inner bag to enclose said at least one of microbes, fungi and other organisms and food substrate within the interior of the inner bag; and joining the first and second walls of the outer bag together at the second end of the outer bag to enclose the inner bag within the interior of the outer bag.

15. The method of claim 14, wherein:

the end portions of the first and second walls of the outer bag at the second end of the outer bag are initially folded back upon themselves so that the first and second walls of the inner bag at the second end of the inner bag project beyond the second end of the outer bag; and further comprising:

joining the projecting first and second walls of the inner bag together at the second end of the inner bag to close the second end of the inner bag.

16. The method of claim 15, further comprising:

unfolding the end portions of the first and second walls of the outer bag at the second end of the outer bag; and joining the unfolded end portions of the first and second walls of the outer bag together at the second end of the outer bag so that the inner bag is enclosed within the interior of the outer bag.

17. The method of claim 13, wherein:

both first and second walls of the inner bag are each constructed of a layer of water-vapor permeable material.

18. The method of claim 13, wherein:

the side edges of the inner bag are non-coupled to the outer bag.

19. The method of claim 13, wherein:

the water-vapor permeable material has a perm rating of from 5 or greater.

20. The method of claim 13, wherein:

a second end of each of the inner bag and the outer bag are non-coupled together.

* * * * *